（12）United States Patent
White et al.

(10) Patent No.: US 8,612,173 B2
(45) Date of Patent: *Dec. 17, 2013

(54) SIX AXIS MOTION CONTROL APPARATUS

(75) Inventors: Richard P. White, Costa Mesa, CA (US); David Wade, Friendswood, TX (US); Henry Wede, Novi, MI (US)

(73) Assignee: Capture 3D, Inc., Costa Mesa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/551,491

(22) Filed: Jul. 17, 2012

(65) Prior Publication Data

US 2012/0281239 A1 Nov. 8, 2012

Related U.S. Application Data

(63) Continuation of application No. 12/332,543, filed on Dec. 11, 2008, now Pat. No. 8,249,823.

(51) Int. Cl.
*G01B 11/24* (2006.01)

(52) U.S. Cl.
USPC ........................................................ 702/151

(58) Field of Classification Search
USPC .................. 702/95, 104, 145, 150, 151, 183; 382/152; 378/4; 359/203.1
See application file for complete search history.

(56) References Cited

U.S. PATENT DOCUMENTS

| 4,167,066 | A | 9/1979 | Cooper et al. |
| 5,023,895 | A | 6/1991 | McCroskey et al. |
| 5,820,623 | A | 10/1998 | Ng |
| 6,157,450 | A | 12/2000 | Marchese-Ragona et al. |
| 6,483,610 | B1 | 11/2002 | Burns |
| 6,974,964 | B1 | 12/2005 | Wang |
| 7,336,375 | B1 | 2/2008 | Faul et al. |
| 8,249,823 | B2 * | 8/2012 | White et al. ................. 702/151 |
| 2005/0022409 | A1 | 2/2005 | Yamamoto et al. |
| 2007/0268540 | A1 * | 11/2007 | Gaspardo et al. ............ 359/201 |
| 2008/0308718 | A1 | 12/2008 | Kollin |

OTHER PUBLICATIONS

GOM Optical Measuring Techniques, Industrial 3D Measurement Technology; Quality Control and Inspection Utilizing the ATOS 3D Scanner; 15 pages.

* cited by examiner

*Primary Examiner* — Mohamed Charioui
(74) *Attorney, Agent, or Firm* — Stetina Brunda Garred & Brucker

(57) ABSTRACT

A motion control apparatus for measuring and scanning an object. The motion control apparatus includes a base. The motion control apparatus also includes an object support assembly that is coupled to the base. The object support assembly receives the object to be scanned and measured. The motion control apparatus includes a scanner track that extends above from the base. The scanner and object are moveable about multiple axes to position to the scanner with respect to the object for viewing the object by the scanner for obtaining measurements of the object.

5 Claims, 6 Drawing Sheets

SIX AXIS MOTION CONTROL APPARATUS

CROSS-REFERENCE TO RELATED APPLICATIONS

The present application is a continuation patent application of U.S. patent application Ser. No. 12/332,543. Filed on Dec. 11, 2008 now U.S. Pat. No. 8,249,823, the entire contents of which are incorporated herein by reference.

STATEMENT RE: FEDERALLY SPONSORED RESEARCH/DEVELOPMENT

Not Applicable

BACKGROUND

1. Field of the Invention

The present invention relates to a motion control apparatus and more particularly to a six axis motion control apparatus for non-contact scanning of a surface of an object.

2. Description of the Prior Art

Three dimensional scanning is an important component associated with the manufacturing process. Optical three dimensional scanning is accurate and a cost-effective alternative delivering more dimensional information to aid in quality control and process optimization. The ability to provide the designed geometry to meet the designer's intent and achieve the engineering dimensional requirement to deliver the intended fit and functionality is an ongoing challenge during the manufacturing process. Optical three dimensional scanning is based on the principle of triangulation. A sensor unit projects different fringe patterns onto an object to be measured. These patterns may then be recorded by two cameras. Based on the optical image equations, a computer may automatically calculate the three dimensional coordinates. In order to digitally render the object completely, several individual measurements from various views are required. After scanning is completed, a software program may be used to calculate a complete high-resolution polygon mesh of the object surface, creating small triangles in curved and large triangles in flatter areas without diminishing the mesh's accuracy.

Traditionally, in a first article inspection, an inspection plan is created based on the CAD data. This plan defines the features to be measured and their corresponding tolerances. For complex parts, several hundred features may need to be measured. The task of measuring these features can be time-consuming with a tactile measuring device. Even after the measuring is complete and the report is generated it is still difficult to identify the problematic areas and determine corrective action due to the lack of full part information. A new procedure is made possible with the use of a white light volumetric scanner which may be used to create and complete a test plan. The first article of inspection process is expedited via the use of full-field scanning and using full color plot images.

In order to measure, assess and document the inspection of numerous identical parts during sampling checks, production ramp-up and for production control, two additional components are required: a handling device for the sensor or the component and a macro recorder in the software for the automation of measurements, data evaluation, protocol generation and output. The ability to speed the production of a broad range of manufactured parts (from engines to medical devices) is desired.

To obtain a three dimensional scan of a surface of an object, the scanner may be held by an individual. The individual may then begin scanning the surface of the object from a variety of different perspectives and angles to achieve a comprehensive scan of the object. However, scanning and measuring an object by having an operator holding the scanner is tedious, time consuming, and not conducive to repetition. To overcome some of the issues associated with using the scanner, the scanner may be placed on a tripod. The tripod configuration still requires manual movement of the scanner by an operator. But the tripod may improve the operator's ability to repeat certain positions with little discrepancy from past measurements. The problem with using a tripod is the limits of various perspectives that are achieved when scanning an object. Typically, for each new scan, the scanner must be repositioned. To address these problems manufacturers may use various devices that enable some automatic component repositioning. Unfortunately, the scan of the object or work piece with these devices may produce undesired shadows, making completely automated scanning less feasible.

An improved method of obtaining a three dimensional scan involves the use of a coordinate measuring machine (CMM). The CMM may be manually controlled by an operator or computer controlled. A typical CMM may be composed of three different axes that are orthogonal to each other. Each axis has a very accurate scaling system that indicates the precise location of that axis. Using a CMM device is more accurate and results in faster scanning times than a three dimensional scan using a handheld scanner. CMM devices may be combined with white light volumetric scanner's that provide laser scanning. Laser scanning uses laser beams that are projected against the surface of the object to be scanned. Thousands of points are taken and used to validate size and position of the object and to create a three dimensional image of the object. Data is generated and transferred to CAD software to create a three dimensional model of the object. However, even with the technological advances associated with CMM devices, collecting measurement data and manual inspection techniques are very time consuming.

Non-contact scanning systems known in the art may be used to reduce the time required for a three dimensional scan and measurement of an object. As understood, one such non-contact scanning system provides a more comprehensive scan than a three dimensional scan using conventional CMM devices, tripods, or manual operation. The non-contact scanning system provides automation that allows for repeat scanning of similar objects for accuracy. Unfortunately, these scanners may be limited with respect to some of its movements. This may result in less comprehensive scans and measurements of the object with respect to certain perspectives.

Accordingly, there exists a need in the art for a motion control apparatus enabling non-contact three dimensional scanning which addresses one or more of the deficiencies identified above, known in the art or discussed below.

BRIEF SUMMARY

A motion control apparatus for non-contact three dimensional scanning of a surface of an object is provided. The motion control apparatus uses a computer and associated software to automate the measurement of the object to be scanned. The ability to automate scanning of the object produces more accurate, faster, and comprehensive results. The motion control apparatus is used to automate the measurement process for small to mid-size parts. The motion control apparatus is configured to record a measurement plan used to measure the object being scanned. Using the measurement plan, the motion control apparatus is able to repeat the process over and over much quicker than is manually possible by an operator. The motion control apparatus may measure each object in precisely the same way by using the repetitive process of the machine, eliminating the human variability of the operators. The motion control apparatus uses precision engineered servo motors and stages to facilitate movement of the object to be scanned and a scanner for obtaining a plurality of views and perspectives of the object that is measured.

The motion control apparatus includes at least three tracks for linear movement of an object support assembly and a white light volumetric scanner. The tracks may use servo motors, stages, belts, hydraulics, pneumatics, or any other well known technology to move the object support assembly that carries the object to be scanned and the scanner. In addition to linear movement, the object support assembly is configured to rotate between 0 and 360 degrees such that the object may be scanned and measured from various perspectives. The scanner is also configured to rotate about an axis defined by a scanner line of sight. The object support assembly may also be configured to pivot about an axis that is parallel to the linear movement associated with at least one of the tracks. The scanner may also be configured to pivot about an axis that is parallel to the linear movement associated with at least one of the tracks.

In further detail, a first embodiment of the motion control apparatus is described. The motion control apparatus includes a base used to support the various tracks that allow for linear movement relative to the base. The base portion is used to provide the support necessary for carrying an object or a work piece to be scanned and measured. The motion control apparatus also includes an object support assembly that is coupled to the base. The object support assembly receives the object to be scanned and measured. The object support assembly is linearly movable parallel to at least two axes. The object support assembly is also rotatable about a third axis. The three axes about which the object support assembly is movable are all orthogonal to each other.

The motion control apparatus also includes a scanner track that extends vertically from the base. The scanner track has a proximal end and a distal end. The proximal end of the scanner track is attached or coupled to the base portion of the motion control apparatus. The distal end of the scanner track extends away from the base. However, the scanner track may be removed from the base to enable enhanced portability of the motion control apparatus. The motion control apparatus also includes a scanner which is coupled to the scanner track. The scanner track defines a longitudinal axis where the scanner is linearly movable parallel to the longitudinal axis. The scanner also defines a line of sight axis. The line of sight axis extends from the scanner to a point on the object to be scanned. In this regard, the line of sight axis may extend linearly. The scanner is configured to rotate about the line of sight axis. The scanner is coupled to the scanner track using a bracket. The scanner is pivotably coupled to the bracket at a first and a second side of the scanner. The scanner defines a pivot axis which extends horizontally from the first side of the scanner to the second side of the scanner and is orthogonal to the longitudinal axis. The scanner is configured to pivot about the pivot axis.

The motion control apparatus may further include a pair of spaced apart tracks. The pair of spaced apart tracks are coupled to the base. The pair of spaced apart tracks defines a first axis which extends longitudinally relative to the pair of spaced apart tracks. The pair of spaced apart tracks defines a second axis which extends latitudinally relative to the pair of spaced apart tracks. The pair of spaced apart tracks provides a course for back and fourth linear movement parallel to the first axis. The object support assembly is linearly movable parallel to the first axis and the second axis.

The ability of the object support assembly to move parallel to the second axis is enabled by a plate that is coupled to the pair of spaced apart tracks. The plate may include four brackets, wherein two brackets are coupled to each of the spaced apart tracks. The brackets of the plate enable the plate to move linearly and parallel to the first axis. The plate is also supported by the pair of spaced apart tracks that are supported by the base. On top of the plate there is a track that is parallel to the second axis. The object support assembly is coupled to the track on the top surface of the plate. The track on the top surface of the plate facilitates linear movement parallel to the second axis. The linear movement parallel to the first axis is independent of the linear movement parallel to the second axis and vice versa. The object support assembly which is coupled to the track on top of the plate is configured to linearly move parallel to the first axis and the second axis.

The object support assembly defines a third axis which may extend vertically from the center of the object support assembly. The third axis is orthogonal to both the first axis and the second axis. The object support plate is configured to rotate about the third axis. Therefore, the object support plate may move parallel to the first axis and the second axis in addition to rotating about the third axis.

The motion control apparatus includes a fourth axis defined by the scanner track. In particular, the fourth axis extends longitudinally relative to the scanner track. The fourth axis is also parallel to the third axis. The scanner is configured to linearly move along the scanner track and parallel to the fourth axis. The linear movement of the scanner is independent of the movement of the object support plate with respect to the first three axes.

The motion control apparatus includes a fifth axis extending from the scanner in a manner which is parallel to the second axis. The scanner is configured to pivot about the fifth axis. The motion control apparatus includes a sixth axis defined by a line of sight associated with the scanner. The scanner line of sight corresponds to a linear axis adjacent to the direction in which a camera associated with the scanner is projected towards. As a result, the sixth axis is variable depending upon where the scanner is projected towards. The scanner is configured to rotate about the sixth axis.

The six axis motion control apparatus may also include a controller for moving the object support assembly about the first axis, the second axis and the third axis. Additionally, the controller is configured to move the scanner about the fourth axis, the fifth axis and the sixth axis. A software program implemented on a computer in communication with the motion control apparatus to instruct the controller to move the object support assembly and the scanner in accordance with an object measurement plan.

In a second embodiment, a six axis motion control apparatus is provided. The motion control apparatus includes a frame used to support the various tracks associated with the scanning and measuring of an object. The motion control apparatus includes a pair of intersecting tracks coupled to the frame. The pair of intersecting tracks form a cross or T-shape. The scanner of the motion control apparatus is coupled to at least one of the intersecting tracks. The scanner is linearly moveable in at least two axes defined by the pair of intersecting tracks.

The pair of intersecting tracks of the motion control apparatus defines a first axis extending latitudinally and a second axis extending longitudinally. One of the tracks from the pair of intersecting tracks is configured for linear movement parallel to the first axis. As a result, the scanner is also movable parallel to the first axis. The scanner includes an attachment means used to slide the scanner vertically parallel to the second axis. The attachment means connects the scanner to one of the tracks from the pair of intersecting tracks.

The motion control apparatus also includes an object support assembly coupled to the frame. The object support assembly is used to secure the object to be scanned and measured. The object support assembly is linearly movable along a third axis. In addition to the object support assembly moving linearly along the third axis, the object support assembly is rotatable about a fourth axis. A pivoting member mounted to the object support assembly may be pivotable about a fifth axis. A rotary drive bracket may be mounted to the pivoting member. The object to be scanned may be mounted to the rotary drive bracket upon which the object may be rotated about a sixth axis defined by the rotary drive bracket.

In another embodiment, a method for non-contact three dimensional scanning of a surface of an object is provided. The method uses a six axis motion control apparatus having an object support assembly. The object support assembly is configured to support the object to be scanned. The object support assembly is coupled to a track for carrying the object parallel to the track. The motion control apparatus also includes a scanner for scanning and measuring the object. The method begins by receiving the object to be scanned on the object support assembly. The method continues with the selection of a measurement plan. The measurement plan corresponds to a particular object to be scanned and maybe thought of as a set of instructions for automated maneuvering of the motion control apparatus relative to six different axes. The object is then moved to a plurality of positions with respect to the first through sixth axes. The object is scanned with respect to the plurality of positions. The method may conclude with the scanning and measuring with respect to each scanner position for the plurality of positions. The measurement plan used may be based upon a non-automated scan of the object using the motion control apparatus. The non-automated scan of the object is recorded on a computer in communication with the apparatus to facilitate the future scanning and measurement of a substantially similar object.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The above description is given by way of example, and not limitation. Given the above disclosure, one skilled in the art could devise variations that are within the scope and spirit of the invention disclosed herein, including various ways of constructing a motion control apparatus for non-contact three dimensional scanning of a surface of an object. Further, the various features of the embodiments disclosed herein can be used alone, or in varying combinations with each other and are not intended to be limited to the specific combination described herein. Thus, the scope of the claims is not to be limited by the illustrated embodiments.

A motion control apparatus for non-contact three dimensional scanning for use in various applications, including metrology, reference point system (RPS) registration, best-fit registration, first article inspection, automation, reverse engineering, and dimensional verification is disclosed. Objects to be scanned are mounted on a table that is movable relative to three different axes. A scanner is also provided which is movable relative to three different axes.

Figure 1:
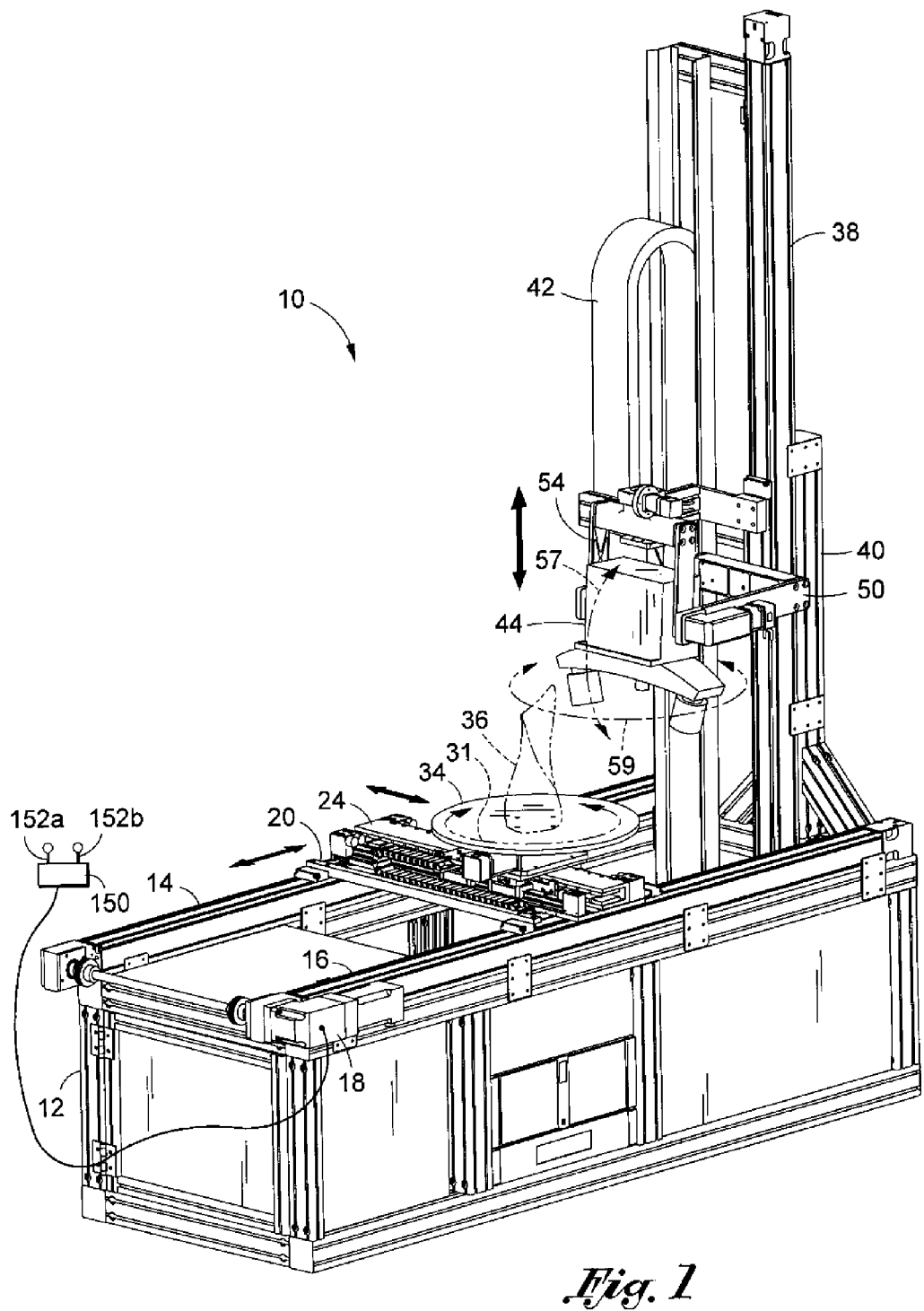
FIG. 1 is a perspective view of a six axis motion control apparatus.

Referring now to FIG. 1, a six axis motion control apparatus 10 constructed in accordance with a first embodiment of the apparatus is provided. The motion control apparatus 10 is used to move an object 36 or work piece to be scanned with respect to a white light volumetric scanner 44. Additionally, the scanner 44 may be moved to capture the object 36 from various perspectives to enable a more comprehensive scan of the object 36. The apparatus 10 is configured for linear motion, rotational motion, and pivoting about a plurality of axes. The apparatus 10 includes a base 12. The base 12 may be formed in the shape of a rectangular box. However, the base 12 is not limited to a rectangular shape and may encompass a variety of different shapes and sizes. A plurality of castors (not shown) may also be coupled to the underside of the base 12 so that the apparatus 10 is portable. The base 12 is used to support the various parts that facilitate movement of the object 36 and the white light volumetric scanner 44. The scanner 44 may be an ATOS 3D Scanner as manufactured by GOM Optical Measuring Techniques incorporated herein by reference. However, other three dimensional white light volumetric scanners may be used with the six axis motion control apparatus 10. Moreover, other types of scanners may be used that are known in the art or developed in the future.

Attached to a top portion of the base 12 is a pair of spaced apart tracks 14 and 16. The pair of spaced apart tracks 14 and 16 is disposed generally parallel to each other. The pair of spaced apart tracks 14 and 16 may each include a slot for receiving a sliding bracket 20 having a rib extending from the underside to facilitate linear movement along the pair of spaced apart tracks 14 and 16. The pair of spaced apart tracks 14 and 16 attached to the top portion of the base 12 is designed to allow for linear movement bi-directionally along the tracks 14 and 16. A motor 18 may be coupled to the tracks 14 and 16 to provide mechanical power to move an item placed on the pair of spaced apart tracks 14 and 16 linearly. The pair of spaced apart tracks 14 and 16 may be coupled to various mechanisms that provide motion control such as the motor 18 and timing belt for traversal of an object support assembly 28 (see FIGS. 3 and 6) along axis 15 (see FIG. 2). It is also contemplated that motion control can be achieved through other means known in the art or developed in the future. For example, the tracks 14 and 16 may alternatively have other mechanisms that control motion such as linear actuator, lead screws, pneumatic mechanisms, hydraulic mechanisms, pulleys, etc. Other motors and timing belts and motion control mechanisms are discussed herein in relation to the other aspects of the motion control apparatus 10. It is contemplated that other motion control mechanisms may be utilized in those situations such as linear actuators, lead screws, pneumatic mechanisms, hydraulic mechanisms, pulleys, etc.

Figure 2:
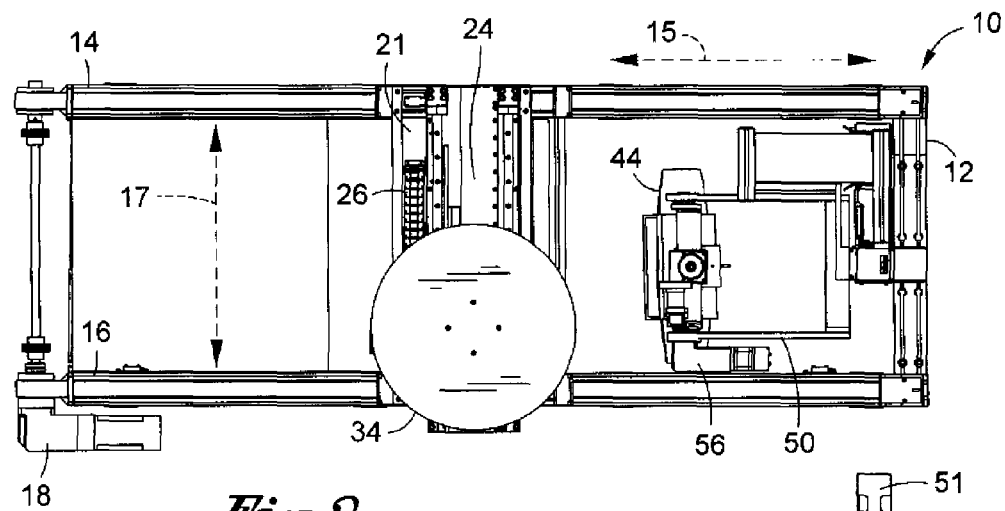
FIG. 2 is an aerial view of the six axis motion control apparatus of FIG. 1.

Referring to FIG. 2, the pair of spaced apart tracks 14 and 16 define two separate axes 15, 17. Extending longitudinally from the pair of spaced apart tracks 14 and 16 is a first axis 15. Extending latitudinally from the pair of spaced apart tracks 14 and 16 is a second axis 17. The first axis 15 and the second axis 17 are perpendicular to each other. Movement along the pair of spaced apart tracks 14 and 16 is linear and parallel to the first axis 15. In this regard, the object 36 that is supported by the base 12 is moved parallel to the first axis 15. It is also contemplated that the base 12 may include only a single track attached to the base 12 that provides for linear movement parallel to the first axis 15.

Figure 6:
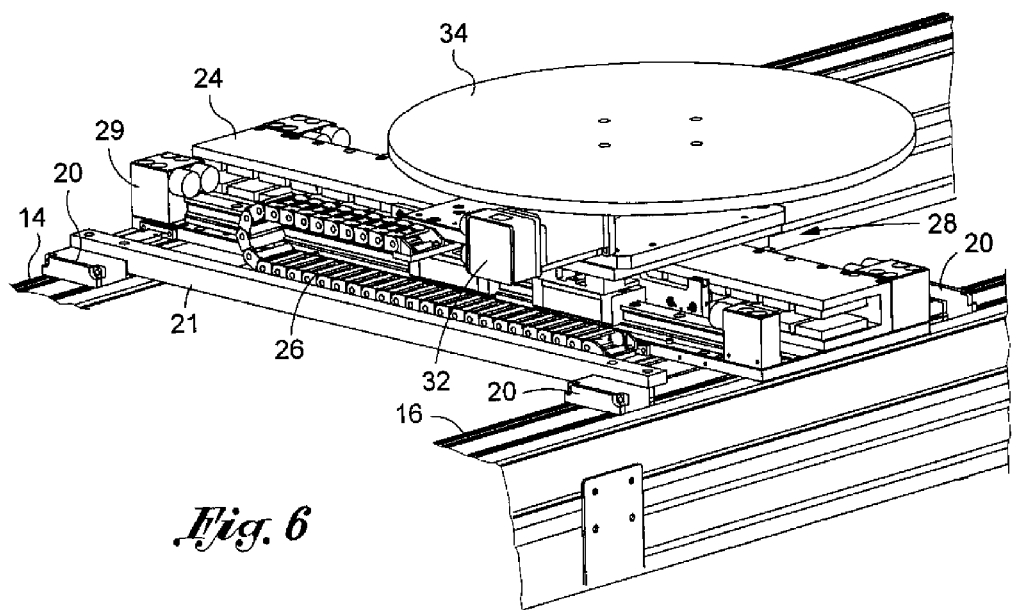
FIG. 6 is a perspective view of an object support assembly.

Referring to FIG. 6, a plate 21 is provided. The plate 21 as shown is rectangular; however, other shapes and sizes may be used to form the plate 21 that is placed on the pair of spaced apart tracks 14 and 16. The rectangular plate 21 includes four sliding brackets 20 coupled to each corner of the rectangular plate 21. Each sliding bracket 20 is configured to be received by the pair of spaced apart tracks 14 and 16. The underside of each sliding bracket 20 may include an extension that is placed in contact with the pair of spaced apart tracks 14 and 16 for facilitating linear movement of the rectangular plate 21 parallel to the first axis 15 (see FIG. 2). The pair of spaced apart tracks 14 and 16 are configured to slidably receive each sliding bracket 20 coupled to the plate 21. As a result, the plate 21 is moved parallel to the first axis 15 through operation of the motor 18 (see FIG. 1) and other motion control mechanisms (e.g., timing belt, lead screw, etc).

On top of the plate 21 is an object support track 24 (see FIG. 6). The object support track 24 is generally parallel to the second axis 17 (see FIG. 2) and configured to receive an object support assembly 28 (see FIGS. 3 and 6) for linear movement along a longitudinal direction of the object support track 24 and parallel to the second axis 17 under the power of a motor 29 (see FIG. 6) and other motion control mechanism such as timing belt, lead screw, linear actuator, etc. Adjacent the object support track 24 on the top surface of the plate 21 is a flexible conduit 26 (see FIG. 6) coupled to the object support assembly 28 for housing cables and the like. The object support assembly 28 is configured to move parallel to the second axis 17 independent of any linear movement of the plate 21 parallel to the first axis 15.

Figure 3:
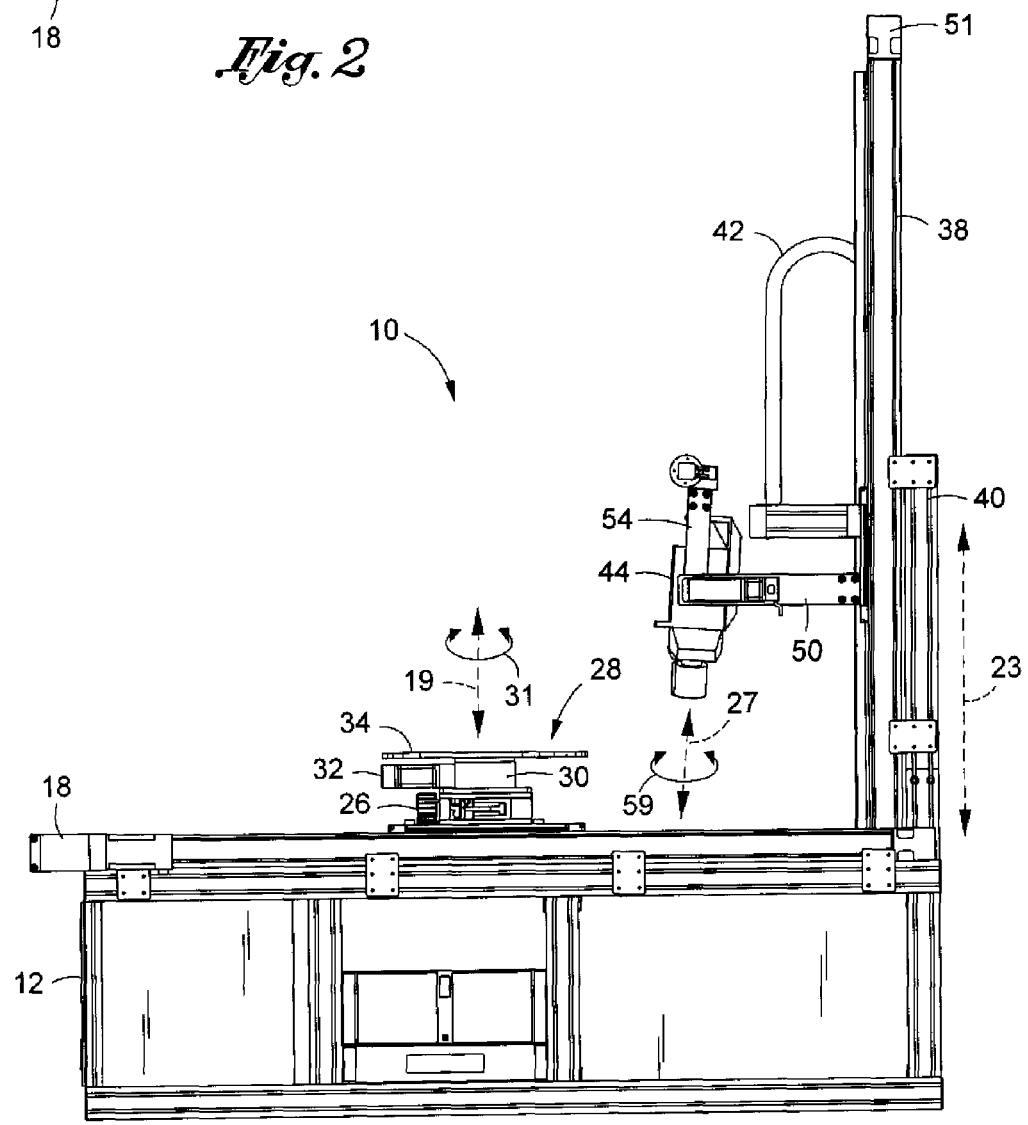
FIG. 3 is a side view of the six axis motion control apparatus of FIG. 1.

Referring now to FIG. 3, the object support assembly 28 includes a rotary drive bracket 30 coupled to the object support track 24. The rotary drive bracket 30 is powered by a motor 32. It is also contemplated that the rotary drive bracket 30 may be powered through other power transmission means such as pneumatic, hydraulic, gears, pulleys, etc. Attached to the top of the rotary drive bracket 30 and also included in the object support assembly 28 is an object support plate 34. The object support plate 34 may be configured in many shapes and sizes. In FIG. 3, the object support plate 34 is circular. The rotary drive bracket 30 may include a central aperture. The central aperture is adapted to receive a shaft (not shown) formed on the under side of the object support plate 34. The shaft may be connected to a gear mechanism, for example, to enable the rotary drive bracket 30 to rotate about a third axis 19. The third axis 19 may be defined by the rotary drive bracket 30 and extend vertically from the object support plate 34. Such a configuration enables rotary movement of the object 36 to be scanned. The rotational movement of the object support plate 34 is independent of the linear movement of the object support assembly 28 with respect to the first axis 15 and the second axis 17.

The third axis 19 (see FIG. 3) is orthogonal to the first axis 15 and the second axis 17. The object support plate 34 is configured to rotate about the third axis 19, as shown by arrow 31 (see FIG. 3). The object support assembly 28 which includes the object support plate 34 coupled to the rotary drive bracket 30 powered by the motor 32, allows for rotation about the third axis 19. The object 36 placed on the object support plate 34 may be rotated between 0 and 360 degrees. Referring back to FIG. 1, when the object 36 to be scanned is placed on top of the object support plate 34 of the object support assembly 28, the object 36 may be moved relative to the first and second axes 15, 17 and rotate about the third axis 19. Also, the object 36 on the object support plate 34 can be traversed relative to a single axis independent of the other axes. Thus, the object 36 placed on the object support plate 34 may move along two linear axes 15, 17 and rotate about the third axis 19 for scanning the object 36 at a plurality of views. The object 36 on the object support plate 34 may be scanned and measured while moving parallel to the first axis 15 and parallel to the second axis 17, and rotating about the third axis 19.

The motion control apparatus 10 also includes a scanner track 38 and a scanner track support 40, as shown in FIGS. 1 and 3. The scanner track support 40 is coupled to the base 12 of the motion control apparatus 10. The scanner track 38 may be attached to the scanner track support 40 using a series of brackets, screws, or other well known affixing means. The scanner track support 40 is used to vertically support the scanner track 38. The scanner track 38 has a proximal end and a distal end. The proximal end of the scanner track 38 may be disposed within the base 12 of the motion control apparatus 10, as shown in FIG. 1. The distal end of the scanner track 38 extends away from the base 12. The scanner track 38 includes slots similar to those described for the pair of spaced apart tracks 14 and 16 described above. The slots are configured to receive an attachment means associated with the scanner 44 to enable linear movement of the scanner 44. The scanner track 38 and the scanner track support 40 are removable from the base 12 portion of the motion control apparatus 10. The ability to remove both the scanner track 38 and the scanner track support 40 enhances the portability of the motion control apparatus 10.

Referring again to FIG. 3, the scanner track 38 defines a fourth axis 23 extending longitudinally with respect to the scanner track 38. The fourth axis 23 is parallel to the third axis 19. The scanner track 38 is configured to facilitate linear movement of a scanner support 50 parallel to the fourth axis 23 via motor 51 and other motion control mechanisms such as a timing belt, lead screw, linear actuator, etc. The scanner support 50 is used to attach the scanner 44 to the scanner track 38. The scanner support 50 may be attached to a sliding bracket having an extension formed on the underside of the sliding bracket to secure the scanner support 50 to the scanner track 38. Coupled to the scanner support 50 is a flexible conduit 42 which holds cables and the like.

Figure 5:
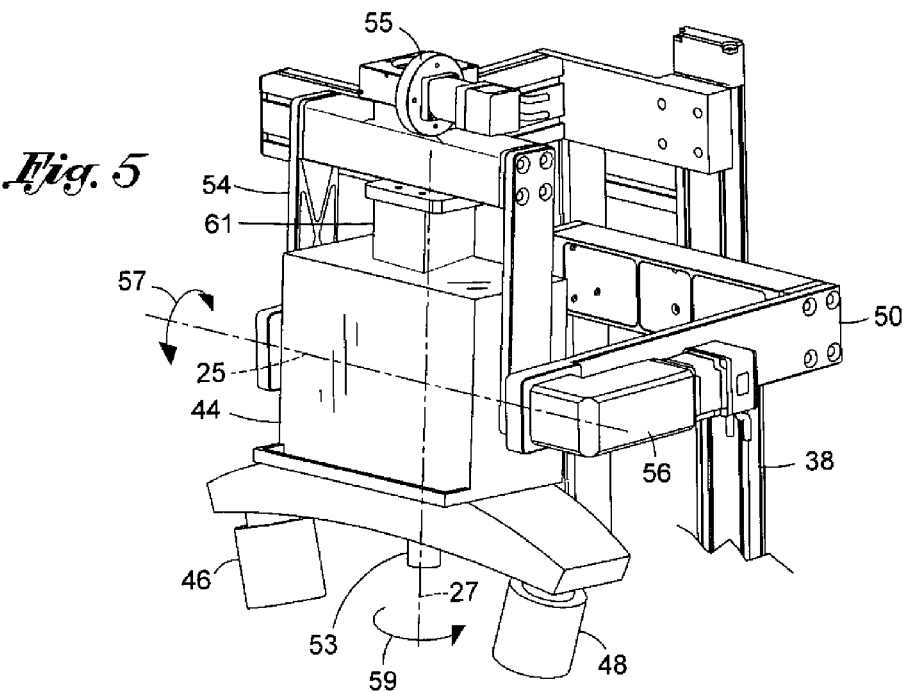
FIG. 5 is a perspective view of a volumetric scanner and a scanner support assembly.

Referring now to FIGS. 3 and 5, the scanner 44 and the scanner support 50 are provided in further detail. The scanner support 50 is generally formed in a U-shape wherein the closed portion of the U-shaped scanner support 50 is attached to the scanner track 38 typically using a sliding bracket. Within the scanner support 50 is another U-shaped bracket 54. The U-shaped bracket 54 is configured to pivot relative to the scanner support 50 which allows the scanner 44 to pivot about the fifth axis 25 under the power of motor 56. Other motion control mechanisms may be used to pivot the scanner 44 about the fifth axis 25 that are known in the art or developed in the future. By way of example and not limitation, the bracket 54 may be pivoted to the support 50 pneumatically, hydraulically, etc. The U-shaped bracket 54 pivots about the fifth axis 25, as shown by arrow 57 (see FIG. 5). The scanner 44 is positioned between the tines of the U-shaped bracket 54 and the tines of the scanner support 50. The base portion or the closed potion of the U-shaped bracket 54 is attached to the top portion of the scanner 44 with a rotary bracket 61 (see FIG. 5) which allows for the scanner 44 to be rotated about a sixth axis 27, as shown by arrow 59 (see FIG. 5). The motor 56 may be coupled to the outer portion of the scanner support 50 to provide the mechanical power being translated from the motor 56 to the U-shaped bracket 54 in order for the bracket 54 to pivot about the fifth axis 25. Another motor 55 may also be coupled to the base portion of the U-shaped bracket 54 to facilitate the rotary movement of the scanner 44 within the U-shaped bracket 54 about the sixth axis 27. The motor 55 may be used in conjunction with other motion control mechanisms that are known in the art or developed in the future. Additionally, the motor 56 may be replaced with other means for providing power such as pneumatic systems, hydraulic systems, etc.

Three dimensional scanners such as scanner 44 provide significant measuring results that are particularly a great benefit for process analysis. The scanner 44 is based on the principle of triangulation. A sensor unit 53 projects different fringe patterns onto the object 36 to be measured. These patterns are then recorded by two cameras 46 and 48. The sensor unit 53 of the scanner 44 includes a line of sight that is directed at the object 36 to be scanned or measured. The line of sight of the sensor unit 53 of the scanner 44 defines the sixth axis 27, wherein the cameras 46 and 48 are configured to rotate about the sixth axis 27, as shown by arrow 59 (see FIG. 5). Although only two cameras are shown, the scanner 44 may have additional cameras (e.g., three or more cameras). The scanner 44 may be a volumetric scanner such as a white light volumetric scanner.

Figure 4:
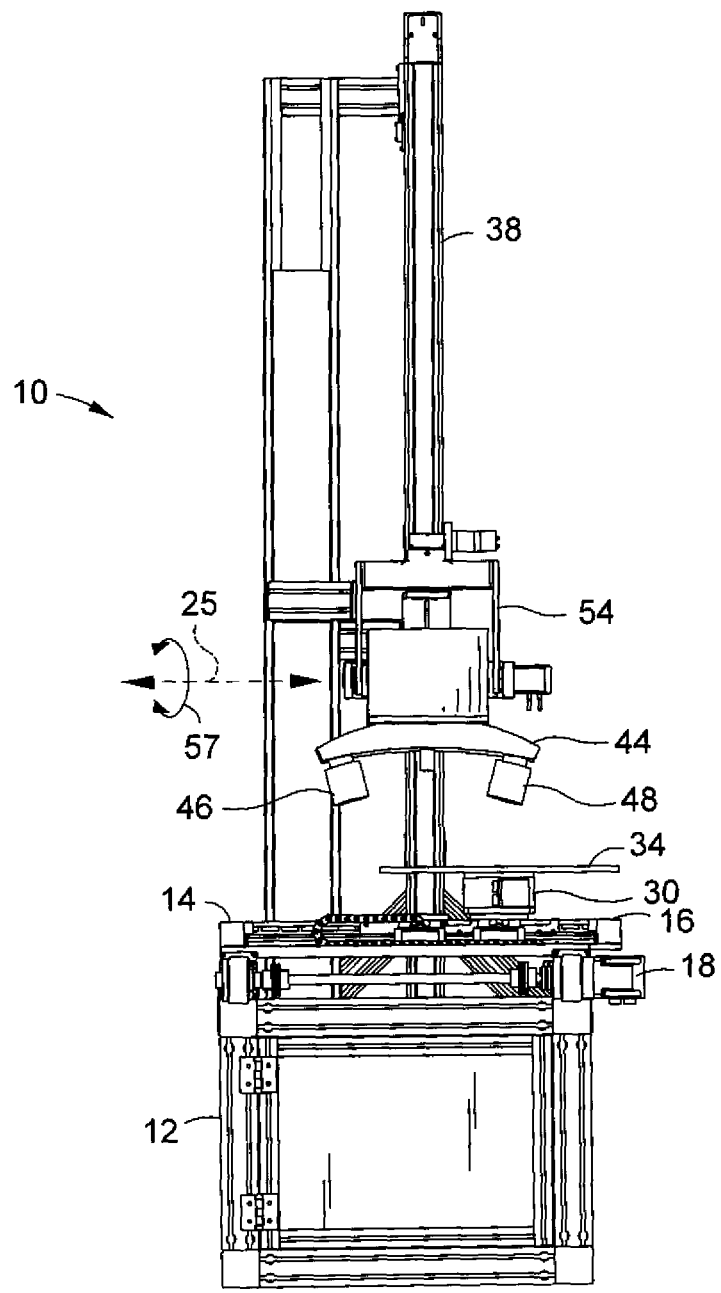
FIG. 4 is a frontal view of the six axis motion control apparatus of FIG. 1.

Referring to FIGS. 4 and 5, the fifth axis 25 extending from the pivot point of the bracket 54 to the scanner support 50 is parallel to the second axis 17 (see FIG. 2). The scanner 44 moves linearly and parallel to the fourth axis 23 (see FIG. 3) as a result of being coupled to the scanner track 38 via the scanner support 50. As discussed above, the scanner 44 is configured to rotate about the sixth axis 27 independent of movement parallel to the fourth axis 23. This allows the scanner 44 to scan objects in the scanner's line of sight while rotating between 0 to 360 degrees to get a more comprehensive scan of the object 36 or the work piece. In addition to the linear movement parallel to the fourth axis 23 and the rotation about the sixth axis 27, the scanner 44 is configured to pivot about the fifth axis 25. In this regard, the scanner 44 is movable with respect to three different axes. The scanner 44 moves linearly along the fourth axis 23, is rotatable about the fifth axis 25, and pivotable about a sixth axis 27. The motion control apparatus 10 provides for six axis motion control. The object support plate 34 is movable with respect to the first three axes 15, 17, 19 and the scanner 44 is movable with respect to the fourth, fifth, and sixth axes 23, 25, 27. The advantage being that the object 36 to be scanned is scannable from various perspectives relative to the six axes described for measurement of the object 36.

Figure 7:
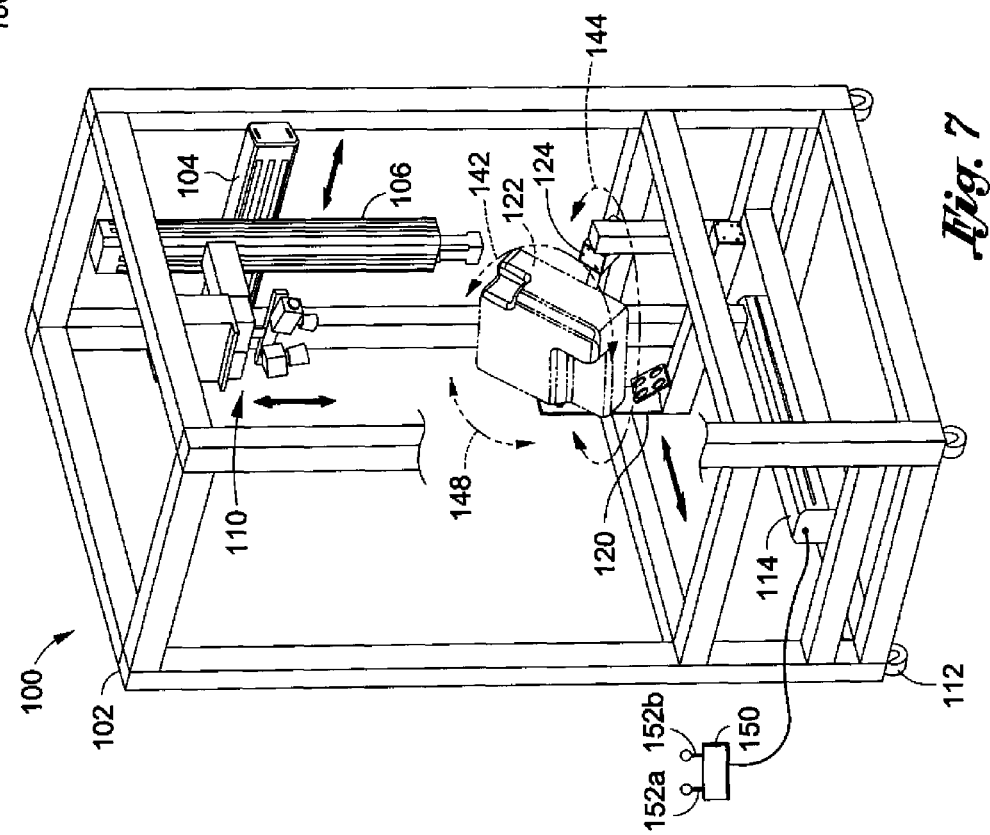
FIG. 7 is a perspective view of a second embodiment of the six axis motion control apparatus.

Referring now to FIG. 7, a second embodiment of the six axis motion control apparatus 100 is provided. The motion control apparatus 100 includes a frame 102. The frame 102 may be constructed from various materials including metal or wood by way of example. The frame 102 may be formed in the shape of a rectangular box. It is contemplated that the frame 102 may be constructed in a variety of shapes and sizes. Attached to the bottom of the frame 102 is a plurality of castors 112, providing portability to the frame 102 of the apparatus 100.

Figure 8:
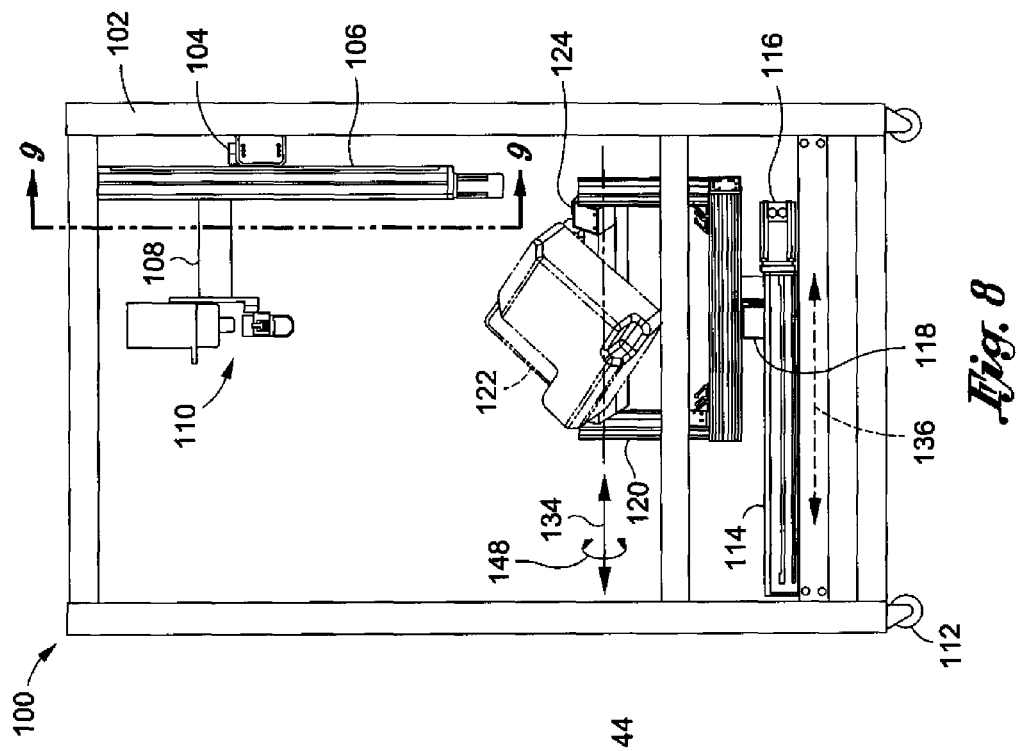
FIG. 8 is a side view of the six axis motion control apparatus of FIG. 7.
Figure 9:
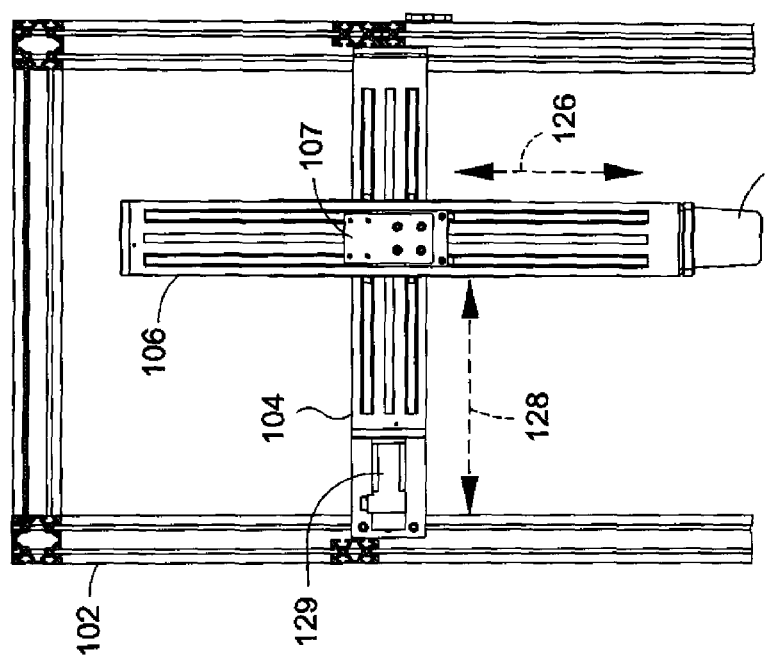
FIG. 9 is a frontal view of a scanner track of the six axis motion control apparatus of FIG. 7.

Referring now to FIG. 9, a first track 104 and a second track 106 are provided. The first track 104 is coupled to opposing bars comprising one side of the frame 102. The first track 104 defines a first axis 128 extending latitudinally. The first track 104 may include a slot or plurality of slots for receiving an extension part from the underside of the second track 106. The extension on the underside of the second track 106 is configured to attach to the slot or slots of the first track 104, such that the second track 106 is securely coupled to the first track 104. The second track 106 may move linearly along the first track 104 and parallel to the first axis 128 under the power of motor 129 and motion control mechanisms such as a timing belt, lead screw, linear actuators, etc. The first track 104 and the second track 106 intersect and are perpendicular to each other. The second track 106 defines a second axis 126 extending longitudinally. The second axis 126 is orthogonal to the first axis 128. The second track 106 may include a sliding bracket 107 configured to receive a scanner support assembly 108 (see FIG. 8). The sliding bracket 107 is configured to move parallel to the second axis 126 under the power of motor 131 and motion control mechanisms such as a timing belt, lead screw, linear actuator, etc.

Referring to FIG. 8, the scanner support assembly 108 is coupled to the second track 106 via the sliding bracket 107. The scanner support assembly 108 moves parallel to the second axis 126 (see FIG. 9). Also, the scanner support assembly 108 may move parallel to the first axis 128 (see FIG. 9). This configuration provides for linear movement of the scanner 110 parallel to two different axes. As a result, the scanner 110 has two degrees of freedom with respect to linear motion.

Figure 10:
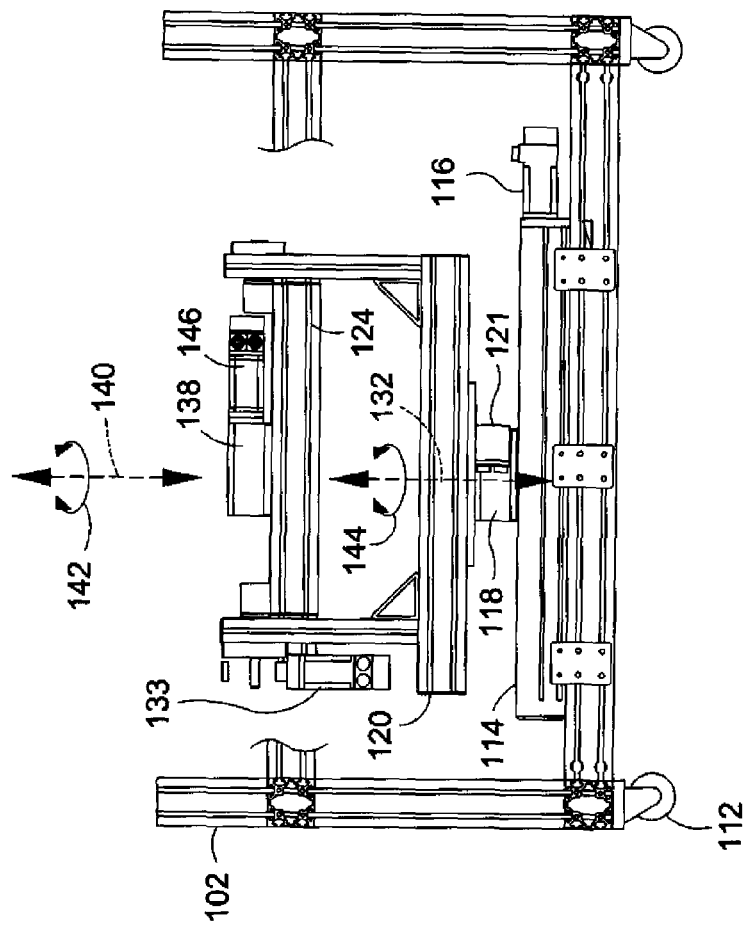
FIG. 10 is a side view of the object support assembly of the six axis motion control apparatus of FIG. 7.

Referring now to FIGS. 7, 8 and 10, an object support assembly 120 is shown. A third track 114 may be attached to the object support assembly 120. The object support assembly 120 is configured to receive an object 122 (see FIG. 8) for scanning and measurement. The third track 114 is coupled to the frame 102 and orthogonal to both the first track 104 (see FIG. 9) and the second track 106 (see FIG. 9). The third track 114 defines a third axis 136 (see FIG. 8) extending longitudinally relative to the third track 114. The third axis 136 extends longitudinally relative to the third track 114. The third axis 136 (see FIG. 8) is orthogonal to the first two axes 126 and 128 (see FIG. 9). The third track 114 may include a slot or a plurality of slots to receive an extension from the underside of a rotary drive bracket 118 (see FIG. 8) for rotating the object support assembly 120 about a fourth axis 132 (see FIG. 10). The object support assembly 120 may move longitudinally along the third axis 136 under power of motor 116 and other motion control mechanisms such as timing belt, lead screw, linear actuator, etc.

The rotary drive bracket 118 may rotate the object support assembly 120 about the fourth axis 132 (see FIG. 10) which extends vertically from the rotary drive bracket 118. The fourth axis 132 may be orthogonal to the third axis 136 (see FIG. 8) and parallel to the second axis 126 (see FIG. 9). The rotary drive bracket 118 may receive power to rotate the object support assembly under power of motor 121 (see FIG. 10) or other power transmission means for providing rotation known in the art or developed in the future. It is contemplated that other well known mechanisms may be used to provide mechanical power for rotation of the rotary drive bracket 118 and linear movement of the object support assembly 120 along the third axis 136.

The object support assembly 120 also includes a pivoting member 124 (see FIGS. 7, 8 and 10) pivotally coupled to the object support assembly 120. The pivoting member 124 defines a fifth axis 134 (see FIG. 8). The pivoting member 124 is configured to pivot about the fifth axis 134 under the power of motor 133 (see FIG. 10) or other power transmission means known in the art or developed in the future. Rotation of the pivoting member 124 is shown by arrow 148 in FIGS. 7 and 8. A second rotary drive bracket 138 may be mounted to the pivoting member 124, as shown in FIG. 10. This permits the object 122 to be rotated about axis 140 (see FIG. 10). Rotation about axis 140 is shown by arrow 142 in FIGS. 7 and 10 and rotation of the support assembly 120 about axis 132 is shown by arrow 144 shown in FIGS. 7 and 10. Similar to the rotary drive bracket 118, the rotary drive bracket 138 mounted to the pivoting member 124 may receive power to rotate the object 122 under power of motor 146 (see FIG. 10) or other power transmission means for providing rotation known in the art or developed in the future. Therefore, when the object 122 or work piece to be scanned and measured is secured to the rotary drive bracket 138, the object 122 may be moved relative to four different axes 136, 132, 134, 140. The object support assembly 120 may move linearly parallel to the third axis 136, rotate about the fourth axis 132, pivot about the fifth axis 134 and rotate about the sixth axis 140. The scanner 110 moves about two separate axes. This allows the motion control apparatus 100 to scan and measure objects 122 with respect to six different axes.

The motion control apparatuses 10, 100 provides an automated measurement process for objects to be scanned. The automated measurement process may be based on a measurement plan. The measurement plan may be configured by manually recording operation of the motion control apparatuses 10, 100 with respect to a particular object that is being measured and the scanner. After the measurement plan is stored in the computer, the motion control apparatuses 10, 100 may be controlled automatically based on the precise coordinates recorded within the measurement plan. The motion control apparatuses 10, 100 increases the number of parts scannable per hour. The motion control apparatuses 10, 100 may repeat the measurement and scanning process without the necessary repetition of manual control by an operator. The motion control apparatuses 10, 100 measures each part in precisely the same way by using the repetitive process, eliminating the variability of different operators. The motion control apparatuses 10, 100 allows for a more comprehensive inspection of the object 36, 122 to be scanned.

In relation to both embodiments, the object to be scanned may be secured to the object support plate 34 or the rotary drive bracket 138. Also, in both embodiments, the object to be scanned and the scanner may be oriented at various angles with a joystick 150 (see FIGS. 1 and 7). The joystick 150 may have two handles 152*a, b*. The handle 152*a* may be in electronic communication with motion control apparatuses 10, 100 for manipulating orientation of the object to be scanned as discussed above. Similarly, the handle 152*b* may be in electronic communication with the motion control apparatuses 10, 100 for manipulating orientation of the scanner 44, 110. The object and scanner are placed at various orientations with respect to each other such that the scanner is capable of scanning the object at a plurality of desired views. It is also contemplated that the joystick may be replaced with a touch pad, mouse or other type of controller.

The apparatuses 10, 100 discussed herein may also have a plurality of sensors operative to determine the exact position of the object to be sensed and the scanner by determining the position of the various brackets and supports for supporting the object and the scanner. The sensors may be proximity sensors, wheel sensors, position sensors or other sensors that are known in the art or developed in the future. In particular, for the first embodiment, a first sensor may sense the position of the object support plate 34 along the first axis 15. A second sensor may sense the position of the object support plate 34 along the second axis 17. A third sensor may sense an angular position of the object support plate 34. A fourth sensor may sense the position of the scanner along the fourth axis 23. A fifth sensor may sense the angular position of the bracket 54 with respect to the support 50. A sixth sensor may sense the angular position of the scanner with respect to the bracket 54. For the second embodiment, six sensors may sense the linear and angular positions of the various components. The sensors may communicate with a computer and provide positional information to the computer for dimensional analysis of the object and other functions.

Initially, the apparatuses 10, 100 may be programmed to scan an object 36, 122. The object may initially be secured to the object support plate 34 or the rotary drive bracket 138. The operator manipulates the object 36, 122 with the handle 152*a* of the joystick 150 such that the object 36, 122 is adjacent to the scanner or is in a scannable position. The operator also manipulates the scanner 44, 110 with the handle 152*b* of the joystick 150 such that the scanner 44, 100 is adjacent to the object 36, 122 to be scanned. In summary, after the object is attached to the object support plate 34 or the rotary drive bracket, the operator translates the object and the scanner to an initial starting position.

The operator moves the object and the scanner with respect to each other such that the scanner can take different views of the object being scanned and to take various dimensional readings off of the object being scanned. With each step, the positions of the object and the scanner are known due to the sensors and recorded in the computer. The information obtained from the scanner to determine the dimension of the object is also associated with the positional information of the object and scanner and stored for analysis. The operator continues the process by further manipulating the object and the scanner into various positions to take multiple dimensional readings of the object by the scanner at a plurality of different views.

The information obtained through the scanning process described above may be analyzed to determine the dimensions of the scanned object. The scanned dimensions of the scanned object may be compared to computer aided drafting based dimensions of the object to determine whether the scanned object is within tolerance or is to be rejected. The operator may complete the scanning process for a sample of objects in a particular lot or scan every object in the lot. The apparatus allows for recording of the various positions of the scanner and the object during the scanning process. Accordingly, the operator may mount the object to the object support plate 34 or the rotary drive bracket 138, then allow the programmed scanning process to repeat the previously recorded steps performed manually by the operator.

Alternatively, the object to be scanned may be the "standard" to which a production run of the object is compared. The first scan of the standard object may determine the dimensions of the standard object. Subsequent objects may be compared to the scanned dimensions of the scanned object either manually or automatically by allowing the apparatus to run the preprogrammed steps manually programmed in by the operator.

It is also contemplated that the initial positions of the object to be scanned and the scanner may be preprogrammed such that the operator need only mount the object to the object support plate 34 or the rotary drive bracket 138.

What is claimed is:

1. A method of non-contact scanning a surface of an object with a motion control apparatus, the method comprising the steps of:
   mounting the object to an object support member of the motion control apparatus;
   manipulating the spatial relationship between a non contact scanner and the object support member for non contact scanning of the surface of the object wherein the non contact scanner is disposed adjacent to the object support member, the manipulating step comprising the steps of:
      traversing the object support member linearly along a first axis and rotateably about a second axis, third axis and a fourth axis;
      traversing the non contact scanner along a straight fifth axis parallel to the second axis and linearly along a sixth axis.

2. The method of claim 1 wherein the non contact scanner is a volumetric scanner.

3. A motion control apparatus for non-contact scanning of a surface of an object, the apparatus comprising:
   an object support member for supporting the object, the object support member rotatable about at least one axis defined by the object support member and linearly traversable along at least one straight longitudinal axis defined by the object support member;
   a non contact scanner for non contact scanning of the surface of the object, the scanner positioned adjacent to the object support member, the scanner being linearly traversable along at least one straight linear axis defined by the scanner;
   wherein a total number of rotational axes of the object support member and the non contact scanner is at least three, and a total number of linear traversal axes of the object support member and the scanner is at least three.

4. The apparatus of claim 3 wherein one straight linear traversal axis of the non contact scanner is parallel to one rotational axis of the object support member.

5. The apparatus of claim 3 wherein the non contact scanner is a volumetric scanner.

\* \* \* \* \*